United States Patent

Commons et al.

Patent Number: 5,968,975
Date of Patent: *Oct. 19, 1999

[54] ELEVATION OF HDL CHOLESTEROL BY 2-[(AMINOTHIOXOMETHYL)-HYDRAZONO]-2-ARYLETHYL CARBAMATES

[75] Inventors: Thomas Joseph Commons, Wayne; Susan Christman, Philadelphia, both of Pa.

[73] Assignee: American Home Products Corporation, Madison, N.J.

[*] Notice: This patent is subject to a terminal disclaimer.

[21] Appl. No.: 09/096,091

[22] Filed: Jun. 11, 1998

Related U.S. Application Data

[60] Provisional application No. 60/049,700, Jun. 16, 1997.
[51] Int. Cl.[6] ............ C07C 255/27; C07C 271/10; A61K 31/27
[52] U.S. Cl. ............ 514/481; 560/24; 560/27; 560/28; 560/29; 560/30; 560/31; 560/33; 560/115; 560/163; 558/445; 514/488; 514/489
[58] Field of Search ............ 558/445; 560/24, 560/30, 29; 546/350; 549/491, 505, 496; 514/481

[56] References Cited

U.S. PATENT DOCUMENTS

4,983,755  1/1991  Bühmann et al. .............. 560/24

FOREIGN PATENT DOCUMENTS

3624349  7/1986  Germany.

OTHER PUBLICATIONS

Russ et al., *Am. J. Med.*, 11:480–493 (1951).
Gofman et al., *Circulation*, 34:679–697 (1966).
Miller and Miller, *Lancet*, 1:16–19 (1975).
Gordon et al., *Circulation*, 79:8–15 (1989).
Stampfer et al., *N. England J. Med.*, 325:373–381 (1991).
Badimon et al., *Lab. Invest..*, 60:455–461 (1989).
Miller et al., *Br. Med. J.*, 282:1741–1744 (1981).
Picardo et al., *Arteriosclerosis.*, 6:434–441 (1986).
Glomset, *J. Lipid Res.*, 9:155–167 (1968).
Glass et al., *Circulation*, vol. 66, Suppl. II 102 (1982).
MacKinnon et al., *J. Biol. Chem.*, 261:2548–2552 (1986).
Grow and Fried, *J. Biol. Chem.*, 253:8034–8041 (1978).
Lagocki and Scanu., *J. Biol. Chem.*, 255:3701–3706 (1978).
Schaefer et al., *J. Lipids Res..*, 23:1259–1273 (1982).
Tomita et al., *J. Heterocyclic Chem.*, 27:707–710 (1990).
Vega and Grundy, *Current Opinion in Lipidology*, 7:209–216 (1996).

Primary Examiner—Robert W. Rausiever
Assistant Examiner—Ebenezer Sackey
Attorney, Agent, or Firm—Michael R. Nagy

[57] ABSTRACT

This invention relates to the treatment of atherosclerosis via raising the level of HDL cholesterol by administration of a compound of the formula

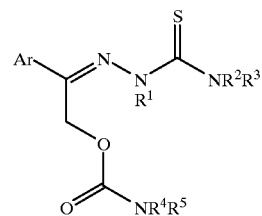

wherein:
$R^1$, $R^2$, and $R^3$ are independently hydrogen, $C_1$–$C_6$ alkyl or —$(CH_2)_{0-6}$Ph where Ph is phenyl optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_6$ alkyl, $C_3$–$C_8$ cycloalkyl, or —$(CH_2)_{0-6}Ar^1$ where $Ar^1$ is phenyl, naphthyl, furanyl, pyridinyl or thienyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl, naphthyl, furanyl, pyridinyl or thienyl or Ar is optionally substituted by halogen, cyano, nitro, $C_1$–$C_6$ alkyl, $C_3$–$C_6$ cycloalkyl, phenyl, $C_1$–$C_6$ alkoxy, phenoxy, trifluoromethyl, $C_1$–$C_6$ alkoxycarbonyl, —$CO_2H$ or OH.

7 Claims, No Drawings

ELEVATION OF HDL CHOLESTEROL BY 2-[(AMINOTHIOXOMETHYL)-HYDRAZONO]-2-ARYLETHYL CARBAMATES

This application claims benefit of priority to provisional patent application No. 60/049,700 filed on Jun. 16, 1997.

FIELD OF INVENTION

This invention relates to compounds useful in elevating high density lipoprotein, the "good" cholesterol. Compounds of this invention increase plasma levels of HDL in a cholesterol fed rat model and as such these compounds may be useful for treating diseases such as atherosclerosis.

BACKGROUND OF THE INVENTION

It is widely believed that HDL is a "protective" lipoprotein [Gloria Lena Vega and Scott Grundy, Current Opinion in Lipidology, 7, 209–216 (1996)] and that increasing plasma levels of HDL may offer a direct protection against the development of atherosclerosis. Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.*, 11 (1951) 480–493; Gofman et al, *Circulation*, 34 (1966) 679–697; Miller and Miller, *Lancet*, 1 (1975) 16–19; Gordon et al., *Circulation*, 79 (1989) 8–15; Stampfer al., *N. Engl. J. Med.*, 325 (1991) 373–381; Badimon et al., *Lab. Invest.*, 60(1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles in humans appears to be correlated to a decreased number of sites of stenosis in the coronary arteries of humans (Miller et al., *Br. Med. J.* 282 (1981) 1741–1744).

There are several mechanisms by which HDL may protect against the progression of atherosclerosis. Studies in vitro have shown that HDL is capable of removing cholesterol from cells (Picardo et al., *Arteriosclerosis*, 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.*, 9 (1968) 155–167). This has been supported by experiments showing efficient transfer of cholesterol from HDL to the liver (Glass et al., *Circulation*, 66 (Suppl. II) (1982) 102; MacKinnon et al., *J. Biol. Chem.*, 261 (1986) 2548–2552). In addition, HDL may serve as a reservoir in the circulation for apoproteins necessary for the rapid metabolism of triglyceride-rich lipoproteins (Grow and Fried, *J. Biol. Chem.* 253 (1978) 1834–1841; Lagocki and Scanu, *J. Biol. Chem.*, 255 (1980) 3701–3706; Schaefer et al., *J. Lipid Res.*, 23 (1982) 1259–1273). Accordingly, agents which increase HDL cholesterol concentrations are useful as anti-atherosclerotic agents, particularly in the treatment of dyslipoproteinemias and coronary heart disease.

BRIEF DESCRIPTION OF THE INVENTION

The compounds of this invention which elevate plasma levels of HDL cholesterol have the general structure

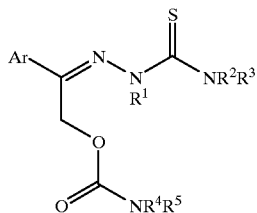

wherein:

$R^1$, $R^2$, and $R^3$ are independently hydrogen, $C_1$–$C_6$ alkyl or —$(CH_2)_{0-6}$Ph where Ph is phenyl optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_6$ alkyl, $C_3$–$C_8$ cycloalkyl, or —$(CH_2)_{0-6}Ar^1$ where $Ar^1$ is phenyl, naphthyl, furanyl, pyridinyl or thienyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl, naphthyl, furanyl, pyridinyl or thienyl or Ar is optionally substituted by halogen, cyano, nitro, $C_1$–$C_6$ alkyl, $C_3$–$C_6$ cycloalkyl, phenyl, $C_1$–$C_6$ alkoxy, phenoxy, trifluoromethyl, $C_1$–$C_6$ alkoxycarbonyl, —$CO_2H$ or OH.

The compounds are tested in vivo in rats fed cholesterol-augmented rodent chow for 8 days according to the test protocol and blood from the rats analyzed for HDL cholesterol.

DETAILED DESCRIPTION OF THE INVENTION

The compounds of this invention are conveniently prepared by the route shown in Scheme I. Specific examples are given in the Experimental Section. These examples are for illustrative purposes only and are not to be construed as limiting to this disclosure in any way. Those skilled in the art will be aware of other methods of preparing compounds of this invention. The starting materials or intermediates are available commercially or can be prepared by standard literature procedures.

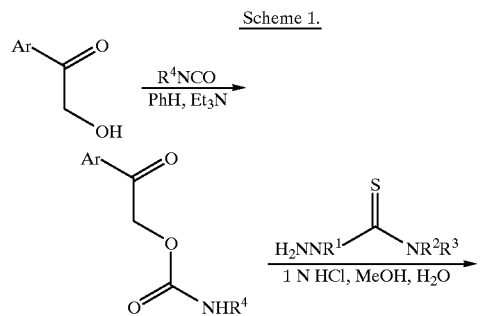

Scheme 1.

3

-continued

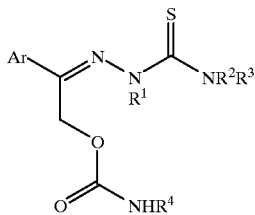

EXPERIMENTAL

Example 1

2-[(Aminothioxomethyl)hydrazono]-2-phenylethyl butylcarbamate (1) A mixture of α-hydroxyacetophenone (10.0 g, 73.4 mmol) and butyl isocyanate (8.27 ml, 73.4 mmol) in 200 ml of chloroform (free of ethanol) was stirred under a nitrogen atmosphere at 60° C. for 6 hours and then overnight at room temperature. The solvent was removed under reduced pressure to give 12.0 g of a yellow solid. Recrystallization of the solid from isopropyl alcohol gave butyl-carbolic acid 2-oxo-2-phenyl-ethyl ester (7.61 g, 44%) as an off-white solid, mp 89–90° C.

Elemental Analysis for $C_{13}H_{17}NO_3$, Calc'd: C, 66.36; H, 7.28; N, 5.95, Found: C, 66.26; H, 7.06; N, 5.84

(2) Thiosemicarbazide (1.162 g, 12.8 mmol) was added to a solution butyl-carbamic acid 2-oxo-2-phenyl-ethyl ester (3.0 g, 12.8 mmol), prepared in the previous step, in 250 ml of methanol plus 2.7 ml of 1N HCl plus 2.5 ml of water and the reaction stirred overnight at room temperature. The solvent was removed under reduced pressure to give 4.67 g of an orange foam. Purification of the foam on 400 g of silica gel (230–400 mesh) using EtOAc-$CH_2Cl_2$ as the eluent gave the title compound (1.20 g, 30%) as an off-white solid, mp 103–116° C.

Elemental Analysis for $C_{14}H_{20}N_4O_2S.0.05\ CH_4O$, Calc'd: C, 54.44; H, 6.57; N, 18.07, Found: C, 54.68; H, 6.57; N, 18.23

Example 2

2-[1-Phenyl-2-[[(phenylamino)carbonyl]oxy] ethylidene]hydrazinecarbothioamide (1) In the same manner as described in step 1 of Example 1 and substituting phenyl isocyanate for butyl isocyanate, phenyl-carbamic acid 2-oxo-2-phenyl-ethyl ester (14.89 g, 53%) was isolated as a light yellow solid, mp 146–148° C.

Elemental Analysis for $C_{15}H_{13}NO_3$, Calc'd: C, 70.58; H, 5.13; N, 5.49, Found: C, 70.75; H, 4.95; N, 5.37

(2) Thiosemicarbazide (678 mg, 7.4 mmol) was added to a solution of phenyl-carbamic acid 2-oxo-2-phenyl-ethyl ester (1.9 g, 7.4 mmol), prepared in the previous step, in 250 ml of methanol plus 1.89 ml of 1N HCl plus 1.75 ml of water and the reaction stirred overnight at room temperature. The solvent was removed under reduced pressure. The residue was taken up in methylene chloride and washed multiple times with water. The organic phase was dried ($MgSO_4$) and the solvent removed under reduced pressure to give 2.483 g of a white solid. Purification of the solid on 400 g of silica gel (230–400 mesh) using EtOAc-$CH_2Cl_2$ as the eluent and then recrystallization of the material collected from isopropyl alcohol gave the title compound (1.22 g, 50%) as a white solid, mp 155–165° C.

4

Elemental Analysis for $C_{16}H_{16}N_4O_2S.0.06\ CH_4O$, Calc'd: C, 58.40; H, 4.96; N, 16.96, Found: C, 58.22; H, 4.89; N, 16.81

Example 3

2-[1-Phenyl-2-[[(cyclohexylamino)carbonyl]oxy] ethylidene]hydrazinecarbothioamide (1) In the same manner as described in step 1 of Example 1 and substituting cyclohexyl isocyanate for butyl isocyanate, cyclohexyl-carbamic acid 2-oxo-phenyl-ethyl ester was isolated as a yellow solid (4.05 g, 42%) after recrystallization of the crude reaction product from methanol, mp 145–148° C.

Elemental Analysis for $C_{15}H_{19}NO_3$, Calc'd: C, 68.94; H, 7.33; N, 5.36, Found: C, 68.87; H, 7.56; N, 5.37

(2) In the same manner as described in step 2 of Example 2, the title compound was isolated as a yellow solid (1.1 g, 23%) after recrystallization of the crude reaction product from isopropyl alcohol, mp 156–159° C.

Elemental Analysis for $C_{16}H_{22}N_4O_2S$, Calc'd: C, 57.46; H, 6.63; N, 16.75, Found: C, 57.71; H, 6.71; N, 16.58

Example 4

2-[(Aminothioxomethyl)hydrazono]-2-phenylethyl (1-methylethyl) carbamate (1) A mixture of α-hydroxyacetophenone (7.0 g, 51.4 mmol), isopropyl isocyanate (10.1 ml, 102.8 mmol) and triethylamine (7.2 ml, 51.4 mmol) in 150 ml of benzene was refluxed under nitrogen overnight. The reaction was diluted with benzene, extracted with 1N HCl, dried ($MgSO_4$) and the solvent removed under reduced pressure to 9.741 g of a brown solid. Recrystallization of the solid from isopropyl alcohol gave isopropyl-carbamic acid 2-oxo-2-phenyl-ethyl ester (4.2 g, 38%) as yellow solid, mp 108–110° C.

Elemental Analysis for $C_{12}H_{15}NO_3$, Calc'd: C, 65.14; H, 6.83; N, 6.33, Found: C, 65.14; H, 6.73; N, 6.44

(2) Thiosemicarbazide (1.44 g, 15.8 mmol) was added to a solution of isopropyl-carbamic acid 2-oxo-2-phenyl-ethyl ester (3.5 g, 15.8 mmol), prepared in the previous step, in 75 ml of methanol plus 4 ml of 1N HCl plus 3.75 ml of $H_2O$ and the mixture stirred at room temperature overnight. The reaction was concentrated under reduced pressure to give a yellow solid. The solid was triturated with methanol, filtered and dried under reduced pressure to give 3.5441 g of a yellow solid. Recrystallization of the solid from isopropyl alcohol gave 1.6402 g (35%) of the title compound as a light yellow solid, mp 74–78° C.

Elemental Analysis for $C_{13}H_{18}N_4O_2S$, Calc'd: C, 52.82; H, 6.25; N, 18.76, Found: C, 52.35; H, 6.18; N, 18.77

Example 5

2-[(Aminothioxomethyl)hydrazono]-2-phenylethyl (phenylmethyl) carbamate (1) A mixture of α-hydroxyacetophenone (7.0 g, 51.4 mmol) and benzyl isocyanate (7.62 ml, 61.7 mmol) in 150 ml of benzene was refluxed under nitrogen for 4.5 hours. An additional 6.35 ml (51.4 mmol) of benzyl isocyanate was added and the reaction refluxed for 22 hours. An additional 6.0 ml (48.6 mmol) of benzyl isocyanate was added and the reaction refluxed overnight. The reaction was extracted with 1N HCl, dried ($MgSO_4$) and the solvent removed under reduced pressure to give 3.81 g of a yellow solid. Recrystallization of the solid from isopropyl alcohol gave benzyl-carbamic acid 2-oxo-2-phenyl-ethyl ester (2.85 g, 21%) as a white solid, mp 110–112° C.

Elemental Analysis for $C_{16}H_{15}NO_3$, Calc'd: C, 71.36; H, 5.62; N, 5.20, Found: C, 71.34; H, 5.56; H, 5.26

(2) Thiosemicarbazide (897 mg, 9.85 mmol) was added to a solution of benzyl-carbamic acid 2-oxo-2-phenyl-ethyl ester (2.6515 g, 9.85 mmol), prepared in the previous step, in 150 ml of methanol plus 2.7 ml of 1N HCl plus 2.5 ml of water and the reaction stirred at room temperature overnight. The solvent was removed under reduced pressure to give a white solid. Recrystallization of the solid from isopropyl alcohol gave 2.5324 g (75%) of the tide compound as a light yellow solid, mp 149–150° C.

Elemental Analysis for $C_{17}H_{18}N_4O_2S$, Calc'd: C, 59.63; H, 5.30; N, 16.36, Found: C, 59.63; H, 5.31; N, 16.15

Example 6

2-[[(Methylamino)thioxomethyl]hydrazono]-2-phenylethyl(1-methylethyl) carbamate

(1) 4-Methyl-3-thiosemicarbazide (2.38 g, 22.6 mmol) was added to a mixture of isopropyl-carbamic acid 2-oxo-2-phenyl-ethyl ester (5.0 g, 22.6 mmol), prepared in step 1 of Example 4, in 70 ml of methanol plus 6 ml of 1N HCl plus 6 ml of water and the reaction stirred at room temperature overnight. The reaction was concentrated under reduced pressure to remove the methanol. The residue was partitioned between methylene chloride and water. The organic layer was separated, washed with water, dried ($MgSO_4$) and the solvent removed under reduced pressure to give 6.545 g of an off-white solid. Recrystallization of the solid from isopropyl alcohol gave 3.8751 g (56%) of the title compound as a white solid, mp 140–141° C.

Elemental Analysis for $C_{14}H_{20}N_4O_2S$, Calc'd: C, 54.52; H, 6.54; N, 18.17, Found: C, 54.52; H, 6.50; N, 18.23

Example 7

2-[(Aminothioxomethyl)hydrazono]-2-(4-chlorophenyl)ethyl(1-methylethyl) carbamate

(1) [Bis(trifluoroacetoxy)iodo]benzene (55.6 g, 129.2 mmol) was added to 4'-chloroacetophenone (10 g, 64.6 mmol) in a mixture of 400 ml of acetonitrile plus 80 ml of water and 11.5 ml of trifluoroacetic acid and the reaction refluxed for approximately 6 hours. The reaction was concentrated under reduced pressure to remove the acetonitrile and the residue partitioned between methylene chloride and water. The organic phase was separated, washed with saturated $NaHCO_3$, dried ($MgSO_4$) and the solvent removed under reduced pressure to give 7.37 g of a tan solid. The solid was first triturated with hexane and the resulting solid recrystallized from isopropyl alcohol to give 4.3 g of 2-hydroxy-1-(4-chloro-phenyl)-ethanone as an off-white solid, mp 124–126° C.

Elemental Analysis for $C_8H_7ClO_2$, Calc'd: C, 56.33; H, 4.14; N, 0.00, Found: C, 56.43; H, 4.21; N, 0.21

(2) A mixture of 2-hydroxy-1-(4-chloro-phenyl)-ethanone (4.7914 g, 28 mmol), prepared in the previous step, isopropyl isocyanate (4.1 ml, 42 mmol) and triethylamine (2.83 ml, 28 mmol) in 100 ml of benzene was refluxed under nitrogen for approximately 24 hours. The solid formed was collected by filtration and dried under high vacuum to give 3.5184 g (49%) of isopropyl-carbamic acid 2-(4-chloro-phenyl)-2-oxo-ethyl ester as an off-white solid. Recrystalli-zation of a portion of this solid from isopropyl alcohol gave an analytically pure sample, mp 163–164° C.

Elemental Analysis for $C_{12}H_{14}ClNO_3$, Calc'd: C, 56.37; H, 5.52; N, 5.48, Found: C, 56.08; H, 5.41; N, 5.41

(3) Thiosemicarbazide (1.4 g, 15.2 mmol) was added to a solution of isopropyl-carbamic acid 2-(4-chloro-phenyl)-2-oxo-ethyl ester (3.26 g, 12.7 mmol), prepared in the previous step, in 200 ml of methanol plus 3 ml of 1N HCl plus 2.5 ml of water and the reaction stirred for approximately 2 days. The solid present was collected by filtration and dried under high vacuum to give 1.646 g (39%) of the title compound as a white solid, mp 181–182° C.

Elemental Analysis for $C_{13}H_{17}ClN_4O_2S$, Calc'd: C, 47.49; H, 5.21; N, 17.04, Found: C, 47.62; H, 5.31; N, 17.19

Example 8

2-[(Aminothioxomethyl)hydrazono]-2-(4-methylphenyl)-ethyl-(1-methylethyl) carbamate

(1) In the same manner as described in step 1 of Example 7 and substituting 4'-methyl acetophenone for 4'-chloroacetophenone, 2-hydroxy-1-p-tolyl-ethanone was obtained (5.9922 g, 54%) as an off-white solid, mp 83–87° C.

Elemental Analysis for $C_9H_{10}O_2$, Calc'd: C, 71.98; H, 6.71; N, 0.00, Found: C, 70.96; H, 6.53; N, 0.05

(2) A mixture of 2-hydroxy-1-p-tolyl-ethanone (5.6 g, 37 mmol), prepared in the previous step, isopropyl isocyanate (5.5 ml, 56 mmol) and triethylamine (5.16 ml, 37 mmol) in 100 ml of benzene was refluxed under nitrogen for approximately 23 hours. The solvent was removed under reduced pressure. The residue was dissolved in $CH_2Cl_2$ and extracted with 1N HCl. The organic layer was dried ($MgSO_4$) and the solvent removed under reduced pressure to give 8.295 g of an oil. Crystallization of the oil from isopropyl alcohol gave isopropyl-carbamic acid 2-oxo-2-p-tolyl-ethyl ester (2.5267 g, 29%) as a light yellow solid, mp 130–133° C.

Elemental Analysis for $C_{13}H_{17}NO_3$, Calc'd: C, 66.36; H, 7.28; N, 5.95, Found: C, 66.02; H, 7.39; N, 5.93

(3) In the same manner as described in Step 3 of Example 7 the title compound was isolated as a white solid (1.1872 g, 39%) after recrystallization from isopropyl alcohol of the crude solid isolated from the reaction mixture, mp 166–167° C.

Elemental Analysis for $C_{14}H_{20}N_4O_2S$, Calc'd: C, 54.52; H, 6.54; N, 18.17, Found: C, 54.46; H, 6.78; N, 18.30

Example 9

2-[(Aminothioxomethyl)hydrazono]-2-(4-methoxyphenyl)-ethyl-(1-methylethyl) carbamate

(1) In the same manner as described in step 1 of Example 7 and substituting 4'-methoxyacetophenone for 4'-chloroacetophenone, 2-hydroxy-1-(4-methoxy-phenyl)-ethanone (4.7613 g, 43%) was obtained as a tan solid, mp 101–103° C.

Elemental Analysis for $C_9H_{10}O_3$, Calc'd: C, 65.05; H, 6.07; N, 0.00, Found: C, 64.93; H, 6.20; N, 0.25

(2) A mixture of 2-hydroxy-1-(4-methoxy-phenyl)-ethanone (4.57 g, 27.5 mmol), prepared in the previous step, isopropyl isocyanate (4.0 ml, 41 mmol) and triethylamine (2.7 ml, 20 mmol) in 100 ml of benzene was refluxed for 18 hours. An additional 1.4 ml (14 mmol) of isopropyl isocyanate was added and the mixture refluxed for 5 hours. After cooling to room temperature a solid had formed. The solid was collected by filtration and dried under high vacuum to give 2.4854 g of a white solid. The filtrate from the solid was concentrated under reduced pressure. The residue was dissolved in methylene chloride and extracted with 1N HCl. The organic layer was dried (MgSO$_4$) and the solvent removed under reduced pressure to give 4.7 g of a solid. Recrystallization of the solid from isopropyl alcohol gave isopropyl-carbamic acid 2-(4-methoxy-phenyl)-2-oxo-ethyl ester (2.6748 g) as a white solid. The two solids combined gave a yield of 74%, mp 121–122° C.

Elemental Analysis for $C_{13}H_{17}NO_4$, Calc'd: C, 62.14; H, 6.82; N, 5.57, Found: C, 62.00; H, 6.78; N, 5.66

(3) In the same manner as described in step 2 of Example 2 the title compound (2.0884 g, 64%) was isolated as an off-white solid, mp 154–156° C.

Elemental Analysis for $C_{14}H_{20}N_4O_3S$, Calc'd: C, 51.84; H, 6.21; N, 17.27, Found: C, 51.78; H, 6.21; N, 17.26

Example 10

2-[(Aminothioxomethyl)hydrazono]-2-(4-cyclohexyl-phenyl)-ethyl-(1-methylethyl) carbamate (1) In the same manner as described in step 1 of Example 7 and substituting 4'-cyclohexylacetophenone for 4'-chloroacetophenone, 2-hydroxy-1-(4-cyclohexylphenyl)-ethanone was obtained (4.0 g, 25%) as an off-white solid, mp 104–106° C.

Elemental Analysis for $C_{14}H_{18}O_2$, Calc'd: C, 77.03; H, 8.31; N, 0.00, Found: C, 75.58; H, 8.24; N, 0.11

(2) In the same manner as described in step 1 of Example 4, isopropyl-carbamic acid 2-(4-cyclohexyl-phenyl)-2-oxo-ethyl ester (2.62 g, 54%) was obtained as a white solid, mp 111–112° C.

Elemental Analysis for $C_{18}H_{25}NO_3$, Calc'd: C, 71.26; H, 8.30; N, 4.62, Found: C, 71.47; H, 8.30; N, 4.67

(3) In the same manner as described in Example 6 and substituting thiosemicarbazide for 4-methyl-3-thiosemicarbazide, the title compound was obtained (2.945 g, 98%) as a white solid, mp 152–157° C.

Elemental Analysis for $C_{19}H_{28}N_4O_2S$, Calc'd: C, 60.61; H, 7.50; N, 14.88, Found: C, 60.30; H, 7.42; N, 14.72

Example 11

2-[(Aminothioxomethyl)hydrazono]-2-(4-phenoxyphenyl) ethyl(1-methylethyl) carbamate (1) In the same manner as described in step 1 of Example 7 and substituting 4'-phenoxyacetophenone for 4'-chloroacetophenone, 2-hydroxy-1-(4-phenoxyphenyl) ethanone (8.36 g, 51%) was obtained as a white solid after purification of the crude reaction product by chromatography on silica gel (230–400 mesh) using hexane-ethyl acetate as the eluent, mp 67–69° C.

Elemental Analysis for $C_{14}H_{12}O_3$, Calc'd: C, 73.67; H, 5.30; N, 0.00, Found: C, 72.89; H, 5.50; N, 0.14

(2) A mixture of 2-hydroxy-1-(4-phenoxyphenyl) ethanone (7.5 g, 32.9 mmol), prepared in the previous step, isopropyl isocyanate (4.85 ml, 49 mmol) and triethylamine (4.58 ml, 32.9 mmol) in 100 ml of benzene was refluxed under nitrogen for approximately 8 hours and then stirred overnight at room temperature. The solid formed was removed by filtration. The filtrate was extracted with 1N HCl, dried (MgSO$_4$) and the solvent removed under reduced pressure to give 5.24 g of a yellow solid. Recrystallization of the solid from isopropyl alcohol gave 1.9 g (18%) of isopropyl carbamic acid 2-(4-phenoxyphenyl)-2-oxo-ethyl ester as a white solid, mp 89–90° C.

Elemental Analysis for $C_{18}H_{19}NO_4$, Calc'd: C, 69.00; H, 6.11; N, 4.47, Found: C, 68.76; H, 6.13; N, 4.49

(3) In the same manner as described in Example 6 and substituting thiosemicarbazide for 4-methyl-3-thiosemicarbazide, the tide compound was obtained (1.56 g, 65%) as an off-white solid, mp 151–153° C.

Elemental Analysis for $C_{19}H_{22}N_4O_3S$, Calc'd: C, 59.05; H, 5.74; N, 14.50, Found: C, 59.24; H, 5.72; N, 14.28

Example 12

2-[(Aminothioxomethyl)hydrazono]-2-(5-chloro-2-methyl-phenyl)ethyl(1-methylethyl) carbamate (1) In the same manner as described in step 1 of Example 7 and substituting 5'-chloro-2'-methylacetophenone for 4'-chloroacetophenone, 2-hydroxy-1-(5-chloro-2-methylphenyl)-ethanone was obtained (10 g, 62%) as a light tan solid, mp 55–57° C.

Elemental Analysis for $C_9H_9ClO_2$, Calc'd: C, 58.55; H, 4.91; N, 0.00, Found: C, 58.29; H, 4.59; N, 0.57

(2) In the same manner as described in step 1 of Example 4, isopropyl -carbamic acid 2-(5-chloro-2-methyl-phenyl)-ethanone (4.34 g, 45%) was obtained as a light tan solid, mp 67–68° C.

Elemental Analysis for $C_{13}H_{16}ClNO_3$, Calc'd: C, 57.89; H, 5.98; N, 5.19, Found: C, 57.81; H, 5.82; N, 5.16

(3) In the same manner as described in Example 6 and substituting thiosemicarbazide for 4-methyl-3-thiosemicarbazide, the tide compound was obtained (2.01 g, 74%) as an off-white solid, mp 120–122° C.

Elemental Analysis for $C_{14}H_{19}ClN_4O_2S$, Calc'd: C, 49.05; H, 5.59; N, 16.34, Found: C, 49.05; H, 5.59; N, 16.41

Example 13

2-[(Aminothioxomethyl)hydrazono]-2-(4-phenyl-phenyl) ethyl(1-methylethyl) carbamate (1) In the same manner as described in step 1 of Example 7 and substituting 4'-phenylacetophenone for 4'-chloroacetophenone, 2-hydroxy-1-(4-phenyl-phenyl)-ethanone (3.57 g, 22%) was obtained as an off-white solid, mp 130–132° C.

Elemental Analysis for $C_{14}H_{12}O_2$, Calc'd: C, 79.23; H, 5.70; N, 0.00, Found: C, 77.88; H, 5.59; N, 0.03

(2) In the same manner as described in step 2 of Example 11, isopropyl -carbamic acid 2-biphenyl-4-yl-2-oxo-ethyl ester was obtained (4.35 g, 62%) as a light tan solid, mp 133–134° C.

Elemental Analysis for $C_{18}H_{19}NO_3$, Calc'd: C, 72.71; H, 6.44; N, 4.71, Found: C, 72.69; H, 6.25; N, 4.60

(3) In the same manner as described in Example 6 and substituting thiosemicarbazide for 4-methyl-3-thiosemicarbazide, the title compound was obtained (2.86 g, 64%) as a tan solid, mp 173–174° C.

Elemental Analysis for $C_{19}H_{22}N_4O_2S$, Calc'd: C, 60.99; H, 6.18; N, 14.69, Found: C, 60.75; H, 6.07; N, 14.29

Example 14

2-[(Aminothioxomethyl)hydrazono]-2-(4-fluoro-phenyl)ethyl(1-methylethyl) carbamate (1) In the same manner as described in step 1 of Example 7 and substituting 4'-fluoroacetophenone for 4'-chloroacetophenone, 2-hydroxy-1-(4-fluoro-phenyl)-ethanone was obtained (4.12 g, 37%) as an off-white solid, mp 116–117° C.

Elemental Analysis for $C_8H_7FO_2$, Calc'd: C, 62.34; H, 4.58; N, 0.00, Found: C, 61.71; H, 4.66; N, 0.11

(2) In the same manner as described in step 2 of Example 7, isopropyl -carbamic acid 2-(4-fluoro-phenyl)-2-oxo ethyl ester was obtained (2.0 g, 32%) as a white solid, mp 140–141° C.

Elemental Analysis for $C_{12}H_{14}FNO_3$, Calc'd: C, 60.24; H, 5.90; N, 5.85, Found: C, 60.16; H, 6.02; N, 6.04

(3) In the same manner as described in Example 6 and substituting thiosemicarbazide for 4-methyl-3-thiosemicarbazide, the title compound was obtained (1.72 g, 59%) as a white solid, mp 155–156° C.

Elemental Analysis for $C_{13}H_{17}FN_4O_2S.0.57\ C_3H_8O$, Calc'd: C, 50.97; H, 6.27; N, 16.16, Found: C, 50.01; H, 5.47; N, 17.99

Example 15

2-[(Aminothioxomethyl)hydrazono]-2-(3-bromo-phenyl) ethyl(1-methylethyl) carbamate

(1) In the same manner as described in step 1 of Example 7 and substituting 3'-bromoacetophenone for 4'-chloroacetophenone, 2-hydroxy-1-(3-bromo-phenyl)-ethanone was obtained (5.2 g, 32%) as an off-white solid, mp 100–101° C.

Elemental Analysis for $C_8H_7BrO_2$, Calc'd: C, 44.68; H, 3.28; N, 0.00, Found: C, 44.39; H, 3.09; N, 0.08

(2) In the same manner as described in step 1 of Example 4, isopropyl - carbamic acid 2-(3-bromo-phenyl)-2-oxo-ethyl ester was obtained (2.46 g, 35%) as an orange solid, mp 125–129° C.

Elemental Analysis for $C_{12}H_{14}BrNO_3$, Calc'd: C, 48.02; H, 4.70; N, 4.67, Found: C, 48.13; H, 4.33; N, 4.61

(3) In the same manner as described in Example 6 and substituting thiosemicarbazide for 4-methyl-3-thiosemicarbazide, the tide compound was obtained (1.38 g, 94%) as a light yellow solid, mp 138–140° C.

Elemental Analysis for $C_{13}H_{17}BrN_4O_2S.0.05\ CH_2Cl_2$, Calc'd: C, 41.52; H, 4.57; N, 14.84, Found: C, 41.73; H, 4.44; N, 14.56

Example 16

2-[(Aminothioxomethyl)hydrazono]-2-(2-fluoro-phenyl) ethyl(1-methylethyl) carbamate

(1) In the same manner as described in step 1 of Example 7 and substituting 2'-fluroracetophenone for 4'-chloroacetophenone, 2-hydroxy-1-(2-fluoro-phenyl)-ethanone was obtained (3.62 g, 33%) as an off-white solid, mp 51–54° C.

Elemental Analysis for $C_8H_7FO_2$, Calc'd: C, 62.34; H, 4.58; N, 0.00, Found: C, 62.34; H, 4.59; N, 0.38

(2) In the same manner as described in step 1 of Example 4, isopropyl-carbamic acid 2-(2-fluoro-phenyl)-2-oxo-ethyl ester was obtained (2.33 g, 46%) as a light yellow solid after purification of the crude reaction product by chromatography on silica gel (230–400 mesh) using ethyl acetate-methylene chloride as the eluent, mp 70–74° C.

Elemental Analysis for $C_{12}H_{14}FNO_3$, Calc'd: C, 60.24; H, 5.90; N, 5.86, Found: C, 60.20; H, 5.83; N, 5.81

(3) In the same manner as described in step 2 of Example 2, the title compound was obtained (1.70 g, 63%) as an off-white foam, MS, m/e ($M^+$) 312.

Elemental Analysis for $C_{13}H_{17}FN_4O_2S.0.12\ C_4H_8O_2$, Calc'd: C, 50.14; H, 5.61; N, 17.35, Found: C, 49.78; H, 5.51; N, 17.09

PHARMACOLOGY

In Vivo Assay: Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Procedure No. 352, modified for use with ninety-six well microtiter plates. After reconstitution with water the reagent contains 300 U/l cholesterol oxidase, 100 U/l horse radish peroxidase, 0.3 mmoles/l 4-aminoantipyrine and 30.0 mmoles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., *J. Lipid Res.*, 32 (1991) 859–866. 25 μl of serum is injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the per cent of total absorbance. HDL cholesterol concentration, in serum, is calculated as the per cent of total cholesterol as determined by FPLC multiplied by the total serum cholesterol concentration.

TABLE I

| Cholesterol Fed Rat | |
|---|---|
| Example | % Increase in HDL (Dose) |
| Example 1 | 74.8% (50 mg/kg) |
| Example 2 | 83.2% (50 mg/kg) |
| Example 3 | 20.4% (50 mg/kg) |
| Example 4 | 173.2% (50 mg/kg) |
| Example 5 | 80.8% (50 mg/kg) |
| Example 6 | 38.6% (50 mg/kg) |
| Example 7 | 91.1% (50 mg/kg) |
| Example 8 | 18.8% (50 mg/kg) |
| Example 9 | 22.6% (50 mg/kg) |
| Example 10 | 13.6% (5O mg/kg) |
| Example 11 | 82.4% (50 mg/kg) |

TABLE I-continued

Cholesterol Fed Rat

| Example | % Increase in HDL (Dose) |
|---|---|
| Example 12 | 44.3% (50 mg/kg) |
| Example 13 | 84.1% (50 mg/kg) |
| Example 14 | 120.0% (40 mg/kg) |
| Example 15 | 88.5% (50 mg/kg) |
| Example 16 | 92.8% (52 mg/kg) |

PHARMACEUTICAL COMPOSITION

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties In suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from high density lipoprotein insufficiency must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached Precise dosages for oral or parenteral administration will be determined by the administering physician based on experience with the individual subject treated and standard medical principles.

Preferably the pharmaceutical composition is in unit dosage form, e.g., as tablets or capsules. In such form, the composition is sub-divided in unit doses containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A compound of the formula

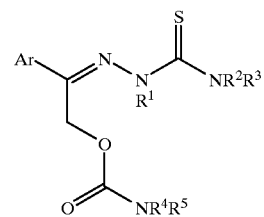

wherein:
R$^1$, R$^2$, and R$^3$ are independently hydrogen, C$_1$–C$_6$ all or —(CH$_2$)$_{0-6}$Ph where Ph is phenyl optionally substituted by halogen, cyano, nitro, C$_1$–C$_6$ alkyl, C$_1$–C$_6$ alkoxy, trifluoromethyl, C$_1$–C$_6$ alkoxycarbonyl, —CO$_2$H or OH;

R$^4$ and R$^5$ are independently hydrogen, C$_1$–C$_6$ alkyl, C$_3$–C$_8$ cycloalkyl, or —(CH$_2$)$_{0-6}$Ar$^1$ where Ar$^1$ is phenyl or naphthyl, and Ar$^1$ may be optionally substituted by halogen, cyano, nitro, C$_1$–C$_6$ alkyl, phenyl, C$_1$–C$_6$ alkoxy, phenoxy, trifluoromethyl, C$_1$–C$_6$ alkoxycarbonyl, —CO$_2$H or OH; and Ar is phenyl or naphthyl, optionally substituted by halogen, cyano, nitro, C$_1$–C$_6$ alkyl, C$_3$–C$_6$ cycloalkyl, phenyl, C$_1$–C$_6$ alkoxy, phenoxy, trifluoromethyl, C$_1$–C$_6$alkoxycarbonyl, —CO$_2$H or OH.

2. A compound according to claim 1 which is 2-[(aminothioxomethyl)hydrazono]-2-phenylethyl(1-methylethyl)carbamate.

3. A compound according to claim 1 selected from the group consisting of:
2-[(aminothioxomethyl)hydrazono]-2-phenylethyl butylcarbamate,
2-[1-phenyl-2-[[(phenylamino)carbonyl]oxy]ethylidene]-hydrazinecarbothioamide,
2-[1-phenyl-2-[[(cyclohexylamino)carbonyl]oxy]ethylidene]hydrazinecarbothioamide,
2-[(aminothioxomethyl)hydrazono]-2-phenylethyl(1-methylethyl) carbamate,
2-[(aminothioxomethyl)hydrazono]-2-phenylethyl (phenylmethyl) carbamate
2-[[(methylamino)thioxomethyl]hydrazono]-2-phenylethyl (1-methylethyl) carbamate,
2-[(aminothioxomethyl)hydrazono]-2-(4-chlorophenyl) ethyl(1-methylethyl) carbamate,
2-[(aminothioxomethyl)hydrazono]-2-(4-methylphenyl)-ethyl(1-methylethyl) carbamate,
2-[(aminothioxomethyl)hydrazono]-2-(4-methoxyphenyl)-ethyl(1-methylethyl) carbamate,
2-[(aminothioxomethyl)hydrazono]-2-(4-cyclohexylphenyl)-ethyl(1-methylethyl) carbamate,
2-[(aminothioxomethyl)hydrazono]-2-(4-phenoxyphenyl) ethyl(1-methylethyl) carbamate,
2-[(aminothioxomethyl)hydrazono]-2-(5-chloro-2-methyl-phenyl) ethyl(1-methylethyl) carbamate,
2-[(aminothioxomethyl)hydrazono]-2-(4-phenyl-phenyl) ethyl(1-methylethyl) carbamate,
2-[(aminothioxomethyl)hydrazono]-2-(4-fluoro-phenyl) ethyl(1-methylethyl) carbamate,
2-[(aminothioxomethyl)hydrazono]-2-(3-bromo-phenyl) ethyl(1-methylethyl) carbamate, and
2-[(aminothioxomethyl)hydrazono]-2-(2-fluoro-phenyl) ethyl(1-methylethyl) carbamate.

4. A method of treating atherosclerosis in mammals which comprises administration to a mammal having atherosclerosis a therapeutically effective amount of a compound of the formula

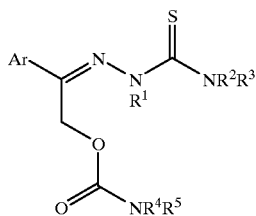

wherein:
$R^1$, $R^2$, and $R^3$ are independently hydrogen, $C_1$–$C_6$ alkyl or —$(CH_2)_{0-6}$Ph where Ph is phenyl optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_6$ alkyl, $C_3$–$C_8$ cycloalkyl, or —$(CH_2)_{0-6}Ar^1$ where $Ar^1$ is phenyl or naphthyl, and $Ar^1$ may be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl or naphthyl, optionally substituted by halogen, cyano, nitro, $C_1$–$C_6$ alkyl, $C_3$–$C_6$ cycloalkyl, phenyl, $C_1$–$C_6$ alkoxy, phenoxy, trifluoromethyl, $C_1$–$C_6$ alkoxycarbonyl, —$CO_2H$ or OH.

5. The method according to claim 4 wherein the therapeutically effective compound used is 2-[(aminothioxomethyl)hydrazono]-2-phenylethyl(1-methylethyl) carbamate.

6. The method according to claim 4 wherein the therapeutically effective compound used is selected from the group consisting of:
2-[(aminothioxomethyl)hydrazono]-2-phenylethyl butylcarbamate,
2-[1-phenyl-2-[[(phenylamino)carbonyl]oxy]ethylidene]-hydrazinecarbothioamide,
2-[1-phenyl-2-[[(cyclohexylamino)carbonyl]oxy]ethylidene]hydrazinecarbothioamide,
2-[(aminothioxomethyl)hydrazono]-2-phenylethyl (phenylmethyl) carbamate,
2-[[(methylamino)thioxomethyl]hydrazono]-2-phenylethyl (1-methylethyl) carbamate,
2-[(aminothioxomethyl)hydrazono]-2-(4-chlorophenyl) ethyl(1-methylethyl) carbamate,
2-[(aminothioxomethyl)hydrazono]-2-(4-methylphenyl)-ethyl(1-methylethyl) carbamate,
2-[(aminothioxomethyl)hydrazono]-2-(4-methoxyphenyl)-ethyl(1-methylethyl) carbamate,
2-[(aminothioxomethyl)hydrazono]-2-(4-cyclohexylphenyl)-ethyl(1-methylethyl) carbamate,
2-[(aminothioxomethyl)hydrazono]-2-(4-phenoxyphenyl) ethyl(1-methylethyl) carbamate,
2-[(aminothioxomethyl)hydrazono]-2-(5-chloro-2-methyl-phenyl) ethyl(1-methylethyl) carbamate,
2-[(aminothioxomethyl)hydrazono]-2-(4-phenyl-phenyl) ethyl(1-methylethyl) carbamate,
2-[(aminothioxomethyl)hydrazono]-2-(4-fluoro-phenyl) ethyl(1-methylethyl) carbamate,
2-[(aminothioxomethyl)hydrazono]-2-(3-bromo-phenyl) ethyl(1-methylethyl) carbamate, and
2-[(aminothioxomethyl)hydrazono]-2-(2-fluoro-phenyl) ethyl(1-methylethyl) carbamate.

7. A pharmaceutical composition comprising a pharmaceutically acceptable carrier and a therapeutically effective amount of a compound of the formula

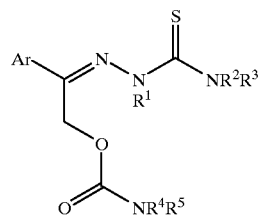

wherein:
$R^1$, $R^2$, and $R^3$ are independently hydrogen, $C_1$–$C_6$ alkyl or —$(CH_2)_{0-6}$Ph where Ph is phenyl optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_6$ alkyl, $C_3$–$C_8$ cycloalkyl, or —$(CH_2)_{0-6}Ar^1$ where $Ar^1$ is phenyl or naphthyl, and $Ar^1$ may be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH; and Ar is phenyl or naphthyl, optionally substituted by halogen, cyano, nitro, $C_1$–$C_6$ alkyl, $C_3$–$C_6$ cycloalkyl, phenyl, $C_1$–$C_6$ alkoxy, phenoxy, trifluoromethyl, $C_1$–$C_6$ alkoxycarbonyl —$CO_2H$ or OH.

* * * * *